United States Patent
Mantegani et al.

[19]

[11] Patent Number: 6,060,483

[45] Date of Patent: May 9, 2000

[54] ANTINEURODEGENERATIVE ERGOLINE DERIVATIVES

[75] Inventors: Sergio Mantegani, Milan; Enzo Brambilla, Mariano Comense; Nicola Carfagna; Mario Varasi, both of Milan, all of Italy

[73] Assignee: Pharmacia & Upjohn S.p.A., Milan, Italy

[21] Appl. No.: 09/147,448

[22] PCT Filed: May 29, 1987

[86] PCT No.: PCT/EP97/02955

§ 371 Date: Dec. 28, 1998

§ 102(e) Date: Dec. 28, 1998

[87] PCT Pub. No.: WO98/00424

PCT Pub. Date: Jan. 8, 1998

[30] Foreign Application Priority Data

Jun. 27, 1996 [GB] United Kingdom ............ 9613571

[51] Int. Cl.[7] ............ A61K 31/48; C07D 457/02
[52] U.S. Cl. ............ 514/288; 546/68; 546/67
[58] Field of Search ............ 514/288; 545/68, 545/67

[56] References Cited

U.S. PATENT DOCUMENTS

| 4,785,001 | 11/1988 | Temperilli et al. | 514/288 |
| 4,839,363 | 6/1989 | Brambilla et al. | 514/288 |
| 4,847,253 | 7/1989 | Buonamici et al. | 514/253 |
| 4,859,678 | 8/1989 | Mantegani et al. | 514/269 |
| 5,210,194 | 5/1993 | Mantegani et al. | 544/361 |
| 5,430,001 | 7/1995 | Tomotsu et al. | 502/113 |

OTHER PUBLICATIONS

Yuzo, M. et al.: Inhibitory action of nicergoline and its major metabolites on acetylcholinesterase activity in rat and mouse brain. Adv. Behav. biol. 38B ( Basic clin. , Ther, Aspects Alzheimer's and parkinson's dis. ), vol. 2, pp. 415–419, 1990.

*Primary Examiner*—John Kight
*Assistant Examiner*—Charanjit S. Aulakh
*Attorney, Agent, or Firm*—Oblon, Spivak, McClelland, Maier & Neustadt, P.C.

[57] ABSTRACT

The present invention provides the new use in the treatment of neurodegenerative diseases with ergoline derivatives of formula (I)

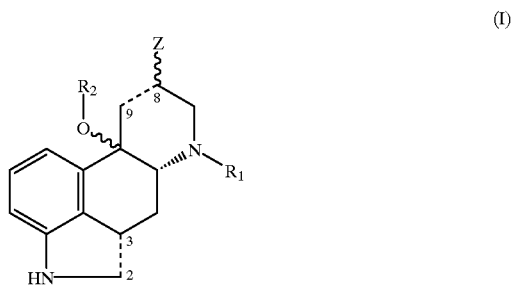

(I)

wherein $R_1$ represents a hydrogen atom or a linear or branched $C_1$–$C_5$ alkyl or $C_2$–$C_5$ alkenyl group optionally substituted with a $C_3$–$C_7$ cycloalkyl, a hydroxy group or a $R_3$-substituted phenyl group wherein $R_3$ is a hydroxy or a hydroxymethyl group; $R_2$ represents a hydrogen atom or a linear or branched $C_1$–$C_5$ alkyl or a $C_2$–$C_5$ alkenyl group optionally substituted with a hydroxy group, or a $R_3$-substituted phenyl group wherein $R_3$ is as above defined, or with a $C_1$–$C_5$ alkoxy group; the symbols—at positions 2,3 and 8, 9 independently denote a single or double chemical bond and Z represents a group $(CH_2)_n OH$, wherein n is 0 or an integer from 1 to 3, or a group $C(R_4)_2 OH$ wherein $R_4$ is a $C_1$–$C_5$ alkyl or a phenyl group, or a pharmaceutically acceptable salt thereof. Some compounds of formula (I) are novel. Processes for their preparation and pharmaceutical compositions containing them are also described.

12 Claims, No Drawings

ANTINEURODEGENERATIVE ERGOLINE DERIVATIVES

This application is a 371 of PCT/EP97/02955 filed May 29, 1997, now WO 98/00424 Jan. 08, 1998.

The present invention relates to the treatment of neurodegenerative diseases employing ergoline derivatives, to new ergoline derivatives for such a treatment, to a process for preparing them and to their pharmaceutical acceptable salts.

The present invention relates to the therapeutic use, in the treatment of neurodegenerative diseases, of ergoline derivatives of formula I

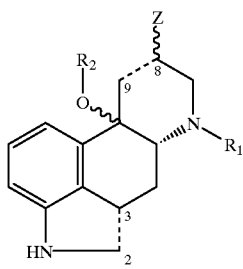

I wherein
$R_1$ represents a hydrogen atom or a linear or branched $C_1$–$C_5$ alkyl or $C_2$–$C_5$ alkenyl group optionally substituted with a $C_3$–$C_7$ cycloalkyl, a hydroxy group or a $R_3$- substituted phenyl group wherein $R_3$ is a hydroxy or a hydroxymethyl group;
$R_2$ represents a hydrogen atom or a linear or branched $C_1$–$C_5$ alkyl or a $C_2$–$C_5$ alkenyl group optionally substituted with a hydroxy group, a $R_3$-substituted phenyl group wherein $R_3$ is as above defined, or with a $C_1$–$C_5$ alkoxy group; the symbols—at positions 2,3 and 8, 9 independently denote a single or double chemical bond and Z represents a group $(CH_2)_nOH$, wherein n is 0 or an integer from 1 to 3, or a group $C(R_4)_2OH$ wherein $R_4$ is a $C_1$–$C_5$ alkyl or a phenyl group, or a pharmaceutically acceptable salt thereof.

The wavy line (~~) in formula I indicates that the substituent in the 8- or 10-position may be either in the α-configuration, i.e. below the plane of the ring, or in the β-configuration, i.e. above the plane of the ring.

In a further aspect of the present invention, there are provided novel ergoline derivatives of formula I as above defined, characterised in that the following compounds are excluded:
6-methyl-8β-hydroxy-10α-methoxy-ergoline,
6-methyl-8β-hydroxymethyl-10β-methoxy-ergoline,
6-methyl-8β-hydroxymethyl-10α-methoxy-ergoline,
6-methyl-8α-hydroxymethyl-10α-methoxy-ergoline,
6-methyl-8β-hydroxymethyl-10α-(1-methylethoxy)-ergoline ,
6-methyl-8β-hydroxymethyl-10α-hydroxy-ergoline,
6-methyl-8β-hydroxymethyl-10β-hydroxy-ergoline,
6-methyl-8β-hydroxymethyl-10α-methoxy-Δ-8,9-ergolene
8β-hydroxymethyl-10α-methoxy-ergoline,
6-methyl-8β-hydroxyethyl-10α-methoxy-ergoline, and
6-methyl-8β-hydroxymethyl-10α-propoxy-ergoline.

More preferably there are provided ergoline derivatives of formula I as above depicted, characterised in that Z is not a hydroxy, hydroxymethyl or hydroxyethyl group, when $R_1$ is hydrogen, or a methyl group, $R_2$ is hydrogen or a methyl, propyl, isopropyl group, —at 2, 3 position is a double bond and—at 8,9 position represents a single or a double bond.

In the present specification, the term $C_1$–$C_5$ alkyl group includes methyl, ethyl, propyl, isopropyl, butyl, isobutyl, pentyl, isopentyl groups and the term $C_2$–$C_5$ alkenyl group includes 2-propenyl, 1-butenyl, 1,1-dimethylallyl, 1-pentenyl, 2-pentenyl. The term $C_3$–$C_6$ cycloalkyl group includes cyclopropyl, cyclopentyl and cyclohexyl groups.

The $R_3$ substituent on the phenyl group in the meanings of $R_1$ and $R_2$ may be in orto, meta or para position.

Pharmaceutical acceptable salts, which may be used in the acid addition salt formation, include maleic, citric, tartaric, fumaric, methanesulphonic, acetic, benzoic, succinic, gluconic, glutamic, malic, mucoic, ascorbic as organic acids or hydrochloric, hydrobromic, sulphuric, or phosphoric as inorganic acids. Among the addition salts obtained by employing acids, hydrochloric, methanesulphonic, citric and tartaric are the most preferred.

In the present invention, $R_1$ is preferably hydrogen atom, methyl, 2 hydroxyethyl or (2-hydroxy-2-phenyl)ethyl group; $R_2$ is preferably hydrogen atom or methyl, 1-methylethyl, propyl, 2-hydroxyethyl, 3-hydroxypropyl, 2-methoxyethyl group, Z is preferably a group $(CH_2)_nOH$, or $C(R_4)_2OH$, n is preferably 0, 1 or 2, $R_4$ is preferably methyl or phenyl group.

Specific examples of the preferred compounds of the present invention are those listed hereinunder:
1) 6-methyl-8β-hydroxy-10α-methoxy-ergoline
2) 6-methyl-8β-hydroxymethyl-10α-methoxy-ergoline,
3) 6-methyl-8α-hydroxymethyl-10α-methoxy-ergoline,
4) 6-methyl-8β-hydroxymethyl-10α-(1-methylethoxy)-ergoline,
5) 6-methyl-8β-hydroxymethyl-10α-hydroxy-ergoline,
6) 6-methyl-8β-hydroxymethyl-10β-hydroxy-ergoline,
7) 6-methyl-8β-hydroxymethyl-10α-methoxy-Δ-8,9-ergolene
8) 8β-hydroxymethyl-10α-methoxy-ergoline,
9) 6-methyl-8β-hydroxy-10α-ethoxy-ergoline,
10) 6-methyl-8β-hydroxy-10α-propoxy-ergoline,
11) 6-methyl-8β-hydroxymethyl-10α-propoxy-ergoline,
12) 8β-hydroxy-10α-methoxy-ergoline,
13) 8β-hydroxy-10β-hydroxy-ergoline,
14) 8α-hydroxy-10α-methoxy-ergoline,
15) 8α-hydroxy-10β-hydroxy-ergoline,
16) 8α-hydroxymethyl-10α-methoxy-ergoline,
17) 8α-hydroxymethyl-10α-hydroxy-ergoline,
18) 6-methyl-8α-hydroxy-10α-methoxy-ergoline,
19) 6-methyl-8α-hydroxymethyl-10α-methoxy-ergoline,
20) 6-methyl-8α-hydroxy-10β-methoxy-ergoline,
21) 6-methyl-8α-hydroxymethyl-10β-methoxy-ergoline,
22) 6-methyl-8β-hydroxy-10β-methoxy-ergoline,
23) 6-methyl-8β-hydroxymethyl-10β-methoxy-ergoline,
24) 6-methyl-8β-(2-hydroxy)ethyl-10α-methoxy-ergoline,
25) 6-methyl-8β-(3-hydroxy)propyl-10α-methoxy-ergoline,
26) 6-methyl-8β-hydroxy-10α-(2-hydroxy)ethoxy-ergoline,
27) 6-methyl-8β-hydroxymiethyl-10α-(2-hydroxy)ethoxy-ergoline,
28) 6-methyl-8β-hydroxy-10α-(3-hydroxy)propoxy-ergoline,
29) 6-methyl-8β-hydroxymethyl-10α-(3-hydroxy)propoxy-ergoline,
30) 6-methyl-8β-hydroxy-10α-(2-methoxy)ethoxy-ergoline,
31) 6-methyl-8β-hydroxymethyl-10α-(2-methoxy)ethoxy-ergoline,
32) (2-hydroxy)ethyl-8β-hydroxy-10α-methoxy-ergoline,
33) (2-hydroxy)ethyl-8β-hydroxymethyl-10α-methoxy-ergoline,
34) (2-hydroxy-2-phenyl)ethyl-8β-hydroxy-10α-methoxy-ergoline 35) (2-hydroxy-2-phenyl)ethyl-8β-hydroxymethyl-10α-methoxy-ergoline,
36) 2,3-dihydro-6-methyl-8β-hydroxy-10α-methoxy-ergoline,
37) 2,3-dihydro-6-methyl-8β-hydroxymethyl-10α-methoxy-ergoline,
38) 2,3-dihydro-6-methyl-8β-(2-hydroxy)ethyl-10α-methoxy-ergoline,
39) 2,3-dihydro-6-methyl-8β-dimethylhydroxymethyl-10α-methoxy-ergoline,
40) 2,3-dihydro-6-methyl-8β-dimethylhydroxymethyl-10α-hydroxy-ergoline,
41) 6-methyl-8β-dimethylhydroxymethyl-10α-methoxy-ergoline,
42) 6-methyl-8β-diethylhydroxymethyl-10α-methoxy-ergoline,
43) 6-methyl-8β-diphenylhydroxymethyl-10α-methoxy-ergoline,
44) 6-methyl-8β-dimethylhydroxymethyl-10α-hydroxy-ergoline,
45) 6-methyl-8β-diethylhydroxymethyl-10α-hydroxy-ergoline,
46) 6-methyl-8β-diphenylhydroxymethyl-10α-hydroxy-ergoline,
47) 6-methyl-8α-dimethylhydroxymethyl-10α-methoxy-ergoline and 6-methyl-8α-diphenylhydroxymethyl-10α-methoxy-ergoline.

The invention provides also a process for preparing compounds of formula I of the present invention, depending on the nature of the substituents, starting from known ergolines by appropriate chemical modifications.

Processes for preparing compounds of formula I and pharmaceutically acceptable salt thereof are as follows:

(i) a preferred process for the preparation of a compound of formula I wherein Z is a hydroxy group and the symbol—at 9, 10 position is a single bond, or a pharmaceutically acceptable salt thereof, comprises
  (1) reacting a compound of formula IIa

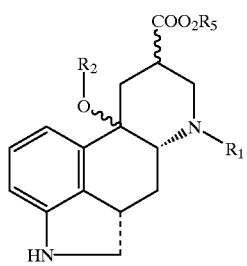

wherein $R_5$ is $C_1$–$C_5$ alkyl group and—and $R_1$ and $R_2$ are defined above, with hydrazine and treating the resultant 8-hydrazide derivative with a nitrite salt in acidic conditions,
  (2) treating the resultant 8-amino derivative of the formula III

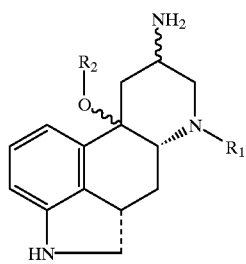

wherein—and $R_1$ and $R_2$ are as defined above, with a nitrite salt in the presence of acetic acid, and hydrolysing the resultant 8-acetyloxy derivative and, if desired,
  (3) converting a resultant compound of formula I

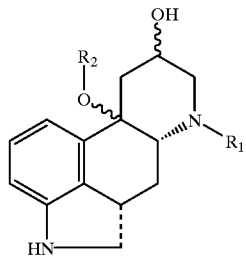

wherein—and $R_1$ are as defined above and $R_2$ is a methyl group, into a compound of formula I wherein $R_2$ is different from methyl, by treatment with a compound of formula $R_2$-OH in the presence of an acid, and, if desired, converting the resultant said compounds of formula I into a pharmaceutically acceptable salt thereof.

(ii) In another example, a preferred process for the preparation of a compound of formula I wherein Z is a group of formula $(CH_2)_n OH$, with n 1 or 2, or a pharmaceutically acceptable salt thereof, comprises
  (1) reducing a compound of formula II

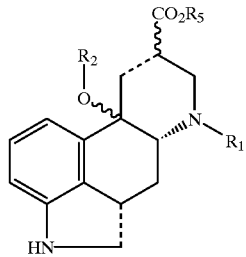

wherein—$R_1$, $R_2$ and $R_5$ are as defined above, and, if desired, (2) treating the resultant compound of formula I, wherein Z represents $CH_2OH$, with methanesulphonylchloride;

(3) reacting the resultant compound of formula IV

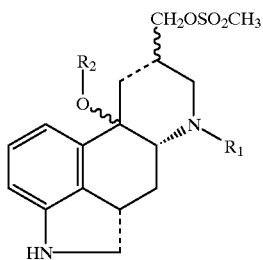
IV wherein $R_1$, $R_2$ and—are as defined above, with KCN, (4) reacting with an acid the resultant compound of formula V

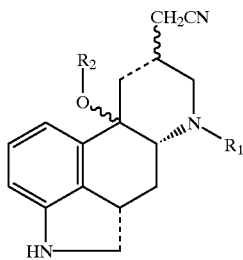
V wherein $R_1$, $R_2$, and—are as defined above, in the presence of an alcohol of the formula $R_5$-OH, wherein $R_5$ is as above defined;

(5) reducing the resultant compound of formula VI

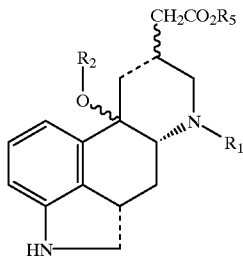
VI wherein $R_1$, $R_2$, $R_5$ and—are as defined above, and, if desired, converting the resultant compound of formula I wherein Z is $CH_2CH_2OH$ or $CH_2OH$, as obtained above under step (ii)(1) into a pharmaceutically acceptable salt thereof.

(iii) In another example, a preferred process for the preparation of a compound of formula I wherein Z is $CH_2CH_2CH_2OH$, or a pharmaceutically acceptable salt thereof, comprises:

(1) condensing a compound of formula IV as defined above with a di-$C_1$–$C_5$ alkylmalonate salt;

(2) heating the resultant compound of formula VII

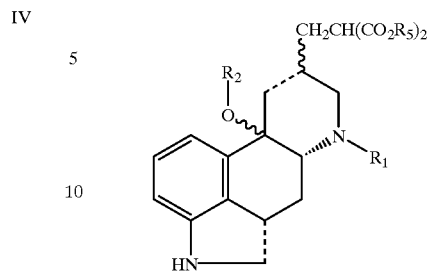
VII wherein $R_1$, $R_2$, $R_5$ and—are as defined above, (3) reducing the resultant compound of formula VIII

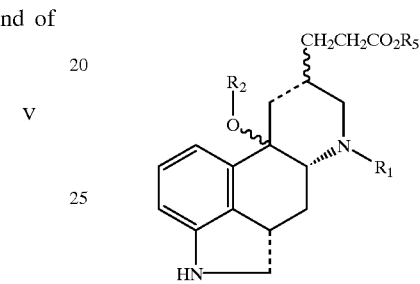
VIII wherein $R_1$, $R_2$, $R_5$ and—are as defined above, and, if desired, converting the resultant compounds of formula I into a pharmaceutically acceptable salt thereof.

(iv) In another example, a preferred process for the preparation of a compound of formula I wherein Z is a group of formula $C(R_4)_2OH$, wherein $R_4$ is as defined above, or a pharmaceutically acceptable salt thereof, comprises:

(1) condensing a compound of formula II as defined above with a Grignard reagent of formula $R_4MgBr$ wherein $R_4$ is as defined above, and, if desired, converting the resultant said compound of formula I into a pharmaceutically acceptable salt thereof.

(v) In a further example, another process for the preparation of a compound of formula I wherein—at 8, 9 position is a single bond, comprises converting a compound of formula IX

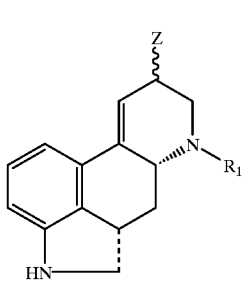
IX wherein—, $R_1$ and Z are as above defined, by photochemical addition of a compound of formula $R_2$-OH, wherein $R_2$ is as above defined, in the presence of an acid, and, if desired, converting the resultant said compounds of formula I into a pharmaceutically acceptable salt thereof.

It should be noted that, if desired, derivatives of formula I produced according to processes (i), (ii), (iii), (iv) and (v) can be further modified at different parts of the molecule by combining processes above described or by means of synthetic procedures known for the ergot derivatives.

The compounds of formula I as defined under (i) above may be prepared for example by reacting a compound of formula IIa, as above defined, with hydrazine hydrate in ethanol at reflux; the corresponding hydrazide was obtained that, by following treatment with sodium nitrite in presence of hydrochloric acid at 0° C. and subsequent heating at 90–100° C., was converted into a compound of general formula III. (P. A. S. Smith, Org. React., 3, 337(1946)).

Subsequent treatment with sodium nitrite in glacial acetic acid at 5–10° C., afforded the corresponding acetyloxy derivative that was then saponified with sodium hydroxide in ethanol or methanol at a temperature ranging from 35° to 70° C. to provide compounds of general formula I. When $R_2$ is a methyl group, these compounds can be converted into compounds of general formula I, wherein $R_2$ is a group different from methyl, by reaction with $R_2$-OH in presence of 10–15% of acids such as sulphuric, trifluoroacetic, methanesulphonic at 10°–35° C.

The compounds of formula I as defined above under (ii) may be prepared for example by reducing a compound of formula II as defined above to afford a compound of general formula I, wherein n is 1. The reduction can be carried out employing reducing agents such as $LiAlH_4$ in solvents such as tetrahydrofuran or dioxane at 0°–50° C., or $NaBH_4$ in solvents such as isopropanol, or methanol at 15°–70° C.

Subsequent reaction of compound of formula I, wherein n is 1, with methanesulphonylchloride in pyridine at 0–5° C., provides compound of formula IV as above defined, that by reaction with KCN in dimethylsulphoxide or dimethylformamide at 50–90° C. affords compound of formula V, as above defined. By reaction of compound of formula V with methanol in presence of gaseous hydrochloric acid, a compound of formula VI was obtained that by reduction as described above provided a compound of formula I wherein n is 2. The compounds of formula I as defined under (iii) may be prepared, for example, condensing a compound of formula IV, as above defined, with sodiumdimethylmalonate in dimethylformamide at 60°–85° C. to afford compound of formula VII, that by heating at 100°–120° C. in dimethylsulphoxide in presence of sodium chloride was converted in compound of formula VIII, further reduction as above described of compound of formula VIII provided compound of formula I wherein n is 3. (C. S. Marvel and F. D. Hager, Org. Synth., 1, 248(1941)).

The compounds of formula I as defined under (iv) may be prepared, for example, condensing a compound of formula II as above defined with a Grignard reagent $R_4MgBr$ in a solvent such as diethylether or tetrahydrofuran at 0°–55° C.(W. W. Moyer and C. S. Marvel, Org. Synth., 2, 602 (1943)). The compounds of formula I as defined under (v) may be prepared, for example, by converting a compound of formula IX as defined above into a compound of formula I by photochemical addition of $R_2OH$ to the double bond in presence of diluted sulphuric acid at 10–40° C. employing Hg/medium pressure lamp.

Some of the starting materials for the preparation of compounds of formula I are known. Other may be analogously prepared starting from known compounds by means of known procedures. The known compounds of formula I are described only as intermediate for the preparation of biological active ergoline compounds in U.S. Pat. No. 3,228,943, EP-A-0 004 664, EP-A-O-156 645 and U.S. Pat. No. 4,861,793, wherein a process for their preparation is also described.

It has been found that the ergoline derivatives of formula I may be unexpectedly used in the treatment of neurodegenerative pathologies associated either with a diminished PKC activity as in the case of Alzheimer's disease or Down' syndrome, age related memory impairment or age related learning disturbances.

The compounds of formula I are able to enhance in vitro the phosphorylation of the endogenous substrate for PKC: B-50/GAP-43 mimicking closely the in vivo situation.

Moreover, the compounds of formula I are able to increase the PKC translocation in synaptosomes of different brain area such as hippocampus and striatum.

The compounds of the present invention could be therefore employed in the treatment of pathologies associated with a reduced functionality of the PKC signal transduction pathway such as various forms of dementia, memory disturbances, Alzheimer's disease and Down's syndrome.

The toxicity of the compounds of the present invention is quite negligible, being >800 mg/Kg p.o., and they are therefore safely employable as useful drugs.

Experimental Part-Biological Data

Phosphorylation of B-50/GAP-43

B-50 purified from rat brain according to Graan T et al. (De Graan P. N. E., Moritz A., De Wit M. and Gispen W. H. Purification of B-50 by 2-mercaptoethanol extraction from rat brain synaptosomal plasma membranes, Neurochem Res 18:875–881, 1993) was utilised as substrate. The protein was phosphorylated by PKC purified according to Kikkawa et al (Kikkawa U., Go M., Kuomoto J. and Nishizuka Y. Rapid purification of PKC by HPLC, Biochim Biophys Res Commun 135:636–643, 1986) (0.012 µg/1 µg substrate/7.5 µM ATP, 1 µCi/tube) in a reaction mixture containing 20 mM Tris Hcl pH 7.0, 10 mM $MgCl_2$, 0.2 mM $CaCl_2$, 1 µg/100 µl PS. γ $^{32}$P-ATP has been utilised as phosphate donor. The incubation was carried out at 30° C. for 5 min., then the reaction was stopped by adding ⅓ volume of a stopping solution containing: 3% Sodium Dodecyl Sulphate (SDS), 5% 2-mercaptoethanol, 10% glycerol, 0.002% bromophenolblue in 0.12 M TrisHCl pH 6.8. Samples were then subjected to one dimensional SDS-Polyacrylamide gel electrophoresis (PAGE) using 11% acrylamide—0.3% bis-acrylamide in the resolving gel. The resulting gel was stained, destained and autoradiographed. Quantitative analysis of B-50 band in the autoradiogram has been performed by densitometric analysis.

| | |
|---|---|
| CONTROL | 100% |
| 6-Methyl-8β-hydroxymethyl-10α-methoxy-ergoline | 108% |

Compounds of the invention are able to increase the in vitro phosphorylation of a specific presynaptic substrate for PKC, the growth associated protein B-50, known to play a key role in different phases of transmission during synaptic plasticity associated events.

PKC Translocation in Different Brain's Area

Purified synaptosomes have been obtained following the procedure described by Dunkley (Dunkley P. R., Health J. W:, Harrison S. M., Jarvie P. E., Glenfield P. J. and Rostas J. A. P. A rapid percolation gradient procedure for isolation of synaptosomes directly from S1 fraction: homogeneity and morphology of subcellular fractions. Brain res 441:59–71, 1988).

Synaptosomes purified from cortex, hippocampus were incubated (10 mg/ml) for 15 min at 30° C. in presence of increasing doses of the compounds of the present invention dissolved in tartaric acid (pH 7.0) or of the vehicle alone. After incubation, purified synaptosomes were collected in cold Krebs buffer containing 10 mM EGTA and then processed according to Shearmann et al (Sheannan M. S., Shinomura T., Oda T. and Nishizuka Y. Protein kinase C subspecies in adult rat hippocampal synaptosomes. Activation by diacylglycerol and arachidonic acid. FEBS Lett 279:261–264, 1991).

Synaptosomes have been lysed in this solution for 30 min at 4° C. with stirring. The lysed suspension was centrifuged at 100000 g for 60 min. The resultant supernatant was processed as "cytosolic fraction". The pellet was again resuspended in lysis buffer containing 0.1% Triton X-100 at 4° C. for 45 min. The centrifugation step was repeated and the resulting supernatant represents the "membrane fraction". Proteins present in the cytosolic and membrane fractions were separated by SDS-PAGE and blotted on nitrocellulose paper. PKC on Western blots was detected with a polyclonal total PKC antibody (Upstate Biotechnology). Western blot analysis of PKC isozymes has been performed utilizing monoclonal antibodies (GIBCO). Antigen antibody complexes were detected by enhanced chemiluminescence. Results have been analysed by computer assisted Image analysis and expressed as per cent of PKC translocation in control conditions.

Data of the PKC translocation in hippocampal synaptosomes of compound of the invention are shown in the following table:

| | |
|---|---|
| CONTROL | 100 |
| 6-Methyl-8β-hydroxymethyl-10α-methoxy-ergoline $10^{-5}$ M | 139 |
| 6-Methyl-8β-hydroxyl-10α-methoxy-ergoline $10^{-5}$ M | 153 |
| 6-Methyl-8β-hydroxymethyl-10β-methoxy-ergoline $10^{-5}$ M | 156 |
| 6-Methyl-8β-hydroxymethyl-10α-hydroxy-ergoline $10^{-5}$ M | 190 |
| 8β-Hydroxymethyl-10α-hydroxy-ergoline $10^{-5}$ M | 190 |
| 6-Methyl-8β-hydroxymethyl-10α-(2-hydroxyethyl)-ergoline $10^{-5}$ M | 162 |
| 6-Methyl-8β-(2-hydroxy)ethyl-10α-methoxy-ergoline $10^{-5}$ M | 193 |

In a physiological assay using purfied and viable synaptosomes, the compounds of the invention are able to increase the translocation of PKC to the membrane compartment. These results are of particular interest considering that the concentration of PKC is significantly reduced in the particulate fraction of various regions of Alzheimer's disease brain) Masliah E., Cole G., Shimohama S., Hansen L., De Teresa R., Terry R. D. and Saitob T. Differential involvement of protein kinase C isozymes in Alzheimer's disease. J Neurosci 10:2113–2124, 1990).

The present invention also includes pharmaceutical composition of compounds of formula I in association with a pharmaceutically acceptable excipient (which can be carrier or diluent). The pharmaceutical composition containing the compounds of the invention are usually prepared following conventional methods and are administered in a pharmaceutically suitable form. For example, the solid oral form may contain, together with the active compound, diluents, e.g. lactose, dextrose, cellulose, corn starch or potato starch; lubricants, e.g. silica, talc, stearic acid, magnesium or calcium stearate, and/or polyethylene glycols; binding agents, e.g. starches, arabic gums, gelatins, methylcellulose or polyvinyl pirrolidone; and, in general, non toxic and inactive substances used in pharmaceutical formulations. These pharmaceutical preparations may be manufactured in known manner, for example, by means of mixing, granulating, tabletting sugar-coated, or film-coating processes.

A tablet formulation may be prepared as follow:

| | Quantity (mg/tablet) |
|---|---|
| ACTIVE INGREDIENT | 25 |
| STARCH DRIED | 425 |
| MAGNESIUM STEARATE | 10 |
| TOTAL | 460 |

The above ingredients are blended together and compressed to form tablets each weighting 460 mg.

The liquid dispersion for oral administration, may be e.g. syrup, emulsions or suspensions. The syrups may contain as carrier, for example, saccharose or saccharose with glycerine and/or mannitol and/or sorbitol. The suspensions and the emulsions may contain as carrier, for example, a natural gum, agar, sodium alginate, pectine or polyvinyl alcohol. The suppositories may contain together with the active compound a pharmaceutically acceptable carrier, e.g. cocoabutter, polyethylen glycol, or lecithin. In general, the drugs may be administered as singler dose or as divided dose so as to provide, say, about 5–50 mg/Kg body weight per day of effective ingredients, preferably 5–15 mg/Kg body weight.

The following examples illustrate the invention

EXAMPLE 1

6-Methyl-8β-(3-hydroxy)propyl-10α-methoxy-ergoline
($R_1$=$CH_3$, $R_2$=$CH_3$, —(2,3)==, —(8,9)=—, Z=$(CH_2)_3OH$)

A stirred mixture of 4.3 g of 6-methyl-8β-tosyloxymethyl-10α-methoxy-ergoline, 2.5 g of sodium diethyl malonate and 1.5 g of potassium iodide in 30 ml of dimethylsulphoxide and 10 ml of diethyl malonate were heated at 75° C. for 2 hours.

The solution was poured in ice water and the resultant precipitate was filtered off, dried and chromatographed on a silica gel column using ethylacetate as eluant. The combined fractions were evaporated to dryness and crystallised from ethanol to give 3.2 g of 2-ethoxycarbonyl-3-(6-methylergolin-10α-methoxy-8β-yl)-propionic acid ethyl ester.

A stirred solution of 15 g of 2-ethoxycarbonyl-3-(6-methylergolin-10α-methoxy-8β-yl)-propionic acid ethyl ester and 15 g of anhydrous sodium chloride in 100 ml of dimethylsulphoxide was heated at 180° C. for 1 hour. The solvent was removed in vacuum and the residue was taken up in ethylacetate and washed several times with brine. After drying and removal of the solvent, the residue was crystallised twice from ethanol to give 11 g of 3-(6-methylergolin-10α-methoxy-8β-yl)-propionic acid ethyl ester.

To a stirred suspension of 5 g of lithium aluminium hydride in 150 ml of tetrahydrofuran was added portionwise 15 g of 3-(6-methylergolin-10α-methoxy-8β-yl)-propionic acid ethyl ester at 25° C.

After stirring for 5 hours, the excess of the hydride was destroyed by carefully addition of 10 ml of water. The suspension was filtered then the solvent was removed.

The residue was dissolved in methanol, charcoalised then crystallised from ethanol to afford 9.6 g of the title compound, m.p.190–195° C.

EXAMPLE 2

6-Methyl-8β-hydroxvmethyl-10α-(2-hydroxy)ethoxy-ergoline
($R_1$=$CH_3$, $R_2$=$CH_2CH_2OH$, —(2,3)==, —(8,9)=—, Z=$CH_2OH$)

A stirred solution of 10 g of 6-methyl-8β-hydroxymethyl-10α-methoxy-ergoline in 100 ml of ethylen glycol was treated with 7.5 ml of concentrated sulphuric acid at room temperature. After stirring for 3 hour, the solution was poured into ice water then made alkaline with concentrated sodium hydroxyde. The precipitated was collected washed with water, and crystallised from ehanol to provide the title compound in 75% yield, m.p. 201–205° C.

EXAMPLE 3
6-Methyl-8β-hydroxymethyl-10α-(2-hydroxy)ethoxy-ergoline
($R_1$=$CH_3$, $R_2$=$CH_2CH_2OH$, —(2,3)==, —(8,9)=—, Z=$CH_2OH$)

Operating as in Example 2, but employing 6-methyl-8α-hydroxymethyl-10α-methoxy-ergoline instead of 6-methyl-8β-hydroxymethyl-10α-methoxy-ergoline, the title compound was obtained in 60% yield, m.p. 178–180° C.

EXAMPLE 4
6-Methyl-8β-hydroxymethyl-10α-(3-hydroxy)propoxy-ergoline
($R_1$=$CH_3$, $R_2$=$CH_2CH_2CH_2OH$, —(2,3)==, —(8,9)=—, Z=$CH_2OH$)

Operating as in Example 2, but employing 1,3-propandiol instead of ethylen glycol, the title compound was obtained in 55% yield, m.p. 189–195° C.

EXAMPLE 5
6-Methyl-8α-(3-hydroxy)protyl-10α-methoxy-ergoline
($R_1$=$R_2$=$CH_3$, —(2,3)==, —(8,9)=—, Z=$(CH_2)_3OH$)

Operating as in Example 1, but employing 6-methyl-8α-tosyloxymethyl-10α-methoxy-ergoline, instead 6-methyl-8β-tosyloxymethyl-10α-methoxy-ergoline, the title compound was obtained in 35% yield, m.p. 134–138° C.

EXAMPLE 6
6-Methyl-8β-(3-hydroxy)propyl-10α-(2-hydroxy)ethoxy-ergoline
($R_1$=$CH_3$, $R_2$=$CH_2CH_2OH$, —(2,3)==, —(8,9)=—, Z=$(CH_2)_3OH$)

Operating as in Example 2, but employing 6-methyl-8β-(3-hydroxy)propyl-10α-methoxy-ergoline instead of 6-methyl-8β-hydroxymethyl-10α-methoxy-ergoline, the title compound was obtained in 57% yield, m.p. 212–215° C.

EXAMPLE 7
6-Methyl-8β-hydroxymethyl-10α-(2-methoxy)ethoxy-ergoline
($R_1$=$CH_3$, $R_2$=$CH_2CH_2OCH_3$, —(2,3)==, —(8,9)=—, Z=$CH_2OH$)

Operating as in Example 2, but employing 2-methoxyethanol instead of ethylen glycol, the title compound was obtained in 67% yield, m.p. 188–193° C.

EXAMPLE 8
6-Methyl-8β-hydroxymethyl-10α-hydroxy-ergoline
($R_1$=$CH_3$, $R_2$=OH, —(2,3)==, —(8,9)=—, Z=$CH_2OH$)

Operating as in Example 2, but employing water instead of ethylen glycol, the title compound was obtain in 85% yield, m.p. 175–179°.

EXAMPLE 9
6-Methyl-8β-hydroxymethyl-10β-hydroxy-ergoline
($R_1$=$CH_3$, R2=OH, —(2,3)==, —(8,9)=—, Z=$CH_2OH$)

From the mother liquor of the preparation of 6-methyl-8β-hydroxymethyl-10α-hydroxy-ergoline, the title compound was recovered in 5% yield, m.p. 134–137° C.

EXAMPLE 10
8β-Hydroxymethyl-10α-hydroxy-ergoline
($R_1$=H, R2=OH, —(2,3)==, —(8,9)=—, Z=$CH_2OH$)

Operating as in Example 8, but employing 8β-hydroxymethyl-10α-methoxy-ergoline instead of 6-methyl-8β-hydroxymethyl-10α-methoxy-ergoline, the title compound was obtained in 65% yield, m.p. 145–149° C.

EXAMPLE 11
8β-Hydroxymethyl-10α-(2-hydroxy)ethoxy-ergoline
($R_1$=H, $R_2$=$CH_2CH_2OH$, —(2,3)==, —(8,9)=—, Z=$CH_2OH$)

Operating as in Example 2, but employing 8β-hydroxymethyl-10α-methoxy-ergoline instead of 6-methyl-8β-hydroxymethyl-10α-methoxy-ergoline, the title compound was obtained in 75% yield, m.p. 198–205° C.

EXAMPLE 12
6-Methyl-8β-dimethylhydroxymethyl-10α-methoxy-ergoline
($R_1$=$CH_3$; $R_2$=$CH_3$, —(2,3)==, —(8,9)=—, Z=$(CH_3)_2COH$)

To a solution of 5 g of 6-methyl-8β-methoxycarbonyl-10α-methoxy-ergoline in 100 ml of tetrahydrofuran were added dropwise 25 ml of 1M solution of methyl magnesium iodide in tetrahydrofuran.

The suspension was refluxed for 2 hours, then treated with 25 ml of a saturated solution of ammonium chloride.

After filtration, the solvent was removed and the residue taken up in dichloromethane, drying, removal of the solvent and subsequent crystallisation from acetone afforded 3.7 g of the title compound, m.p.141–147° C.

EXAMPLE 13
6-Methyl-8β-dimethylhydroxymethyl-10α-(2-hydroxy)ethoxy-ergoline
($R_1$=$CH_3$; $R_2$=$CH_2CH_2OH$, —(2,3)==, —(8,9)=—, Z=$(CH_3)_2COH$)

Operating as in Example 2, but employing 6-methyl-8β-dimethylhydroxymethyl-10α-methoxy-ergoline instead of 6-methyl-8β-hydroxymethyl-10α-methoxy-ergoline, the title compound was obtained in 43% yield, m.p. 178–184° C.

EXAMPLE 14
6-(2-Hydroxy)ethyl-8β-hydroxymethyl-10α-methoxy-ergoline
($R_1$=$CH_3$, $R_2$=$CH2CH_2OH$, —(2,3)==, —(8,9)=—, Z=$CH_2OH$)

To a stirred solution of 3 g of 8β-hydroxymethyl-10α-methoxy-ergoline, 3 g of potassium carbonate in 25 ml of dimethylformamide was added 1.3 g of 2-bromoethanol.

After stirring for 3 hours at room temperature, the solution was diluted with ethylacetate and thoroughly washed with brine, after drying the solvent was removed and the residue chromatographed on a small pad of silica to provide after crystallisation from ethanol 2.1 g of the title compound, m.p. 198–204° C.

EXAMPLE 15
2.3β-dihydro-6-methyl-8β-hydroxymethyl-10α-methoxy-ergoline
($R_1$=$CH_3$, $R_2$=$CH_3$, —(2,3)=—, —(8,9)=—, Z=$CH_2OH$)

To a stirred solution of 5 g of 6-methyl-8β-hydroxymethyl-10α-methoxy-ergoline in 35 ml of trifluoroacetic acid was carefully added portionwise under a stream of nitrogen, 0.7 g of sodiumborohydride.

After 10 minutes of stirring, the solution was diluted with ice water, basified with ammonia and extracted with dichloromethane. After drying and removal of the solvent, the residue was columned on silica gel eluting with chloroform to afford after crystallisation from ethylacetate 1.3 g of the title compound, m.p.134–138° C.

EXAMPLE 16

2,3α-dihydro-6-methyl-8β-hydroxymethyl-10α-methoxy-ergoline ($R_1=CH_3$, $R_2=CH_3$, —(2,3)=—, —(8,9)=—, Z=$CH_2OH$)

The mother liquor of the crystallization of compound 15 were carefully chromatographed on silica gel eluting with chloroform/methanol 9/1, affording after crystallization from isopropanol the title compound, m.p.97–102° C.

We claim:

1. A method of treating neurodegenerative diseases, comprising administering to a patient in need thereof an effective amount of an ergoline derivative represented by formula I:

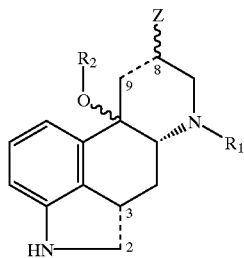

I wherein $R_1$ represents a hydrogen atom or a linear or branched $C_1$–$C_5$ alkyl or $C_2$–$C_5$ alkenyl group optionally substituted with a $C_3$–$C_7$ cycloalkyl, a hydroxy group or a $R_3$-substituted phenyl group wherein $R_3$ is a hydroxy or a hydroxymethyl group;

$R_2$ represents a hydrogen atom or a linear or branched $C_1$–$C_5$ alkyl or a $C_2$–$C_5$ alkenyl group optionally substituted with a hydroxy group, or a $R_3$-substituted phenyl group wherein $R_3$ is above defined, or with a $C_1$–$C_5$ alkoxy group; the symbols—at positions 2, 3 and 8, 9 independently denote a single or double chemical bond and Z represents a group $(CH_2)_nOH$, wherein n is 0 or an integer from 1 to 3, or a group $C(R_4)_2OH$ wherein $R_4$ is a $C_1$–$C_5$ alkyl, or a phenyl group, or a pharmaceutically acceptable salt thereof.

2. The method of claim 1, wherein $R_1$ is a hydrogen atom, methyl, 2 hydroxyethyl or (2-hydroxy-2-phenyl)ethyl group; $R_2$ is hydrogen atom or methyl, 1-methylethyl, propyl, 2-hydroxyethyl, 3-hydroxypropyl, 2-methoxyethyl group, Z is a group $(CH_2)_nOH$, or $C(R_4)_2OH$, n is 0, 1 or 2, $R_4$ is methyl or phenyl group.

3. The method of claim 1, wherein the neurodegenerative diseases are selected from the group consisting of Alzheimer's diseases, Down's syndrome, dementia, and memory impairment.

4. An ergoline derivative formula represented by formula I:

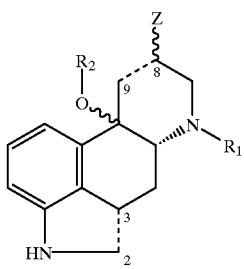

I wherein $R_1$ represents a hydrogen atom or a linear or branched $C_1$–$C_5$ alkyl or $C_2$–$C_5$ alkenyl group optionally substituted with a $C_3$–$C_7$ cycloalkyl, a hydroxy group or a $R_3$-substituted phenyl group wherein $R_3$ is a hydroxy or a hydroxymethyl group;

$R_2$ represents a hydrogen atom or a linear or branched $C_1$–$C_5$ alkyl or a $C_2$–$C_5$ alkenyl group optionally substituted with a hydroxy group, or a $R_3$-substituted phenyl group wherein $R_3$ is above defined, or with a $C_1$–$C_5$ alkoxy group; the symbols—at positions 2, 3 and 8, 9 independently denote a single or double chemical bond and Z represents a group $(CH_2)_nOH$, wherein n is 0 or an integer from 1 to 3, or a group $C(R_4)_2OH$ wherein $R_4$ is a $C_1$–$C_5$ alkyl or a phenyl group, or a pharmaceutically acceptable salt thereof, with the proviso that the following compounds are excluded:

6-methyl-8β-hydroxy-10α-methoxy-ergoline,
6-methyl-8β-hydroxymethyl-10β-methoxy-ergoline,
6-methyl-8β-hydroxymethyl-10α-methoxy-ergoline,
6-methyl-8α-hydroxymethyl-10α-methoxy-ergoline,
6-methyl-8β-hydroxymethyl-10α-(methylethoxy)-ergoline,
6-methyl-8β-hydroxymethyl-10α-hydroxy-ergoline,
6-methyl-8β-hydroxymethyl-10β-hydroxy-ergoline,
6-methyl-8β-hydroxymethyl-10α-methoxy-Δ-8,9-ergoline,
8β-hydroxymethyl-10α-methoxy-ergoline,
6-methyl-8β-hydroxymethyl-10α-methoxy-ergoline, and
6-methyl-8β-hydroxymethyl-10α-propoxy-ergoline.

5. The ergoline derivative of claim 4, wherein Z is not a hydroxy, hydroxymethyl or hydroxyethyl group when $R_1$ is hydrogen, or a methyl, propyl group, $R_2$ is hydrogen or a methyl, propyl, isopropyl group, —at the 2, 3 position is a double bond and—at the 8, 9 position represents a single or a double bond.

6. A process for preparing the ergoline derivative of claim 4, wherein Z is a hydroxy group and the symbol—at 8, 9 position is a single bond, or a pharmaceutically acceptable salt thereof, which comprises:

(1) reacting a compound of formula represented by formula IIa:

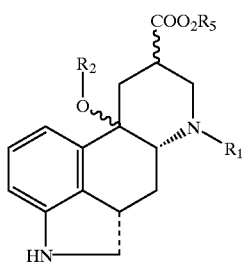

wherein $R_5$ is $C_1$–$C_5$ alkyl group and—and $R_1$ and $R_2$ are as defined in claim 4, with hydrazine, and treating the resulting 8-hydrazide derivative with a nitrite salt in acidic conditions, (2) treating the resulting 8-amino derivative represented by formula III:

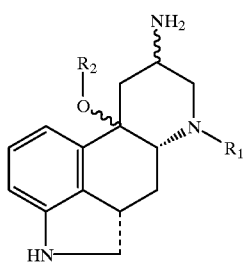

wherein—and $R_1$ and $R_2$ are as defined above, with a nitrite salt in the presence of acetic acid, and hydrolyzing the resultant 8-acetyloxy derivative and, optionally, (3) converting the resulting compound represented by formula I:

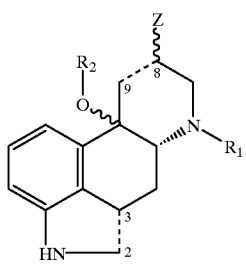

wherein Z is a hydroxy group and the symbol—at 8, 9 position is a single bond, and $R_1$ is as defined above and $R_2$ is methyl group, into a compound represented by formula I wherein $R_2$ is different from methyl, by treating with a compound represented by formula $R_2$-OH in the presence of an acid, and, optionally, converting the resulting compound represented by formula I into a pharmaceutically acceptable salt thereof.

7. A process for preparing the ergoline derivative of claim 4, wherein Z is a group of formula $(CH_2)_nOH$, with n 1 or 2, or a pharmaceutically acceptable salt thereof, which comprises:

(1) reducing a compound represented by formula II:

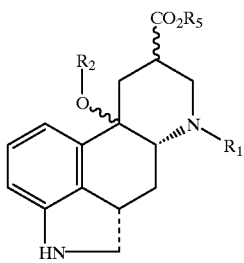

wherein—$R_1$ and $R_2$ are as defined in claim 4, and $R_5$ is $C_1$–$C_5$-alkyl, and, optionally, (2) treating the resulting compound represented by formula I, wherein Z represents $CH_2OH$, with methanesulphonylchloride;

(3) reacting the resulting compound represented by formula IV

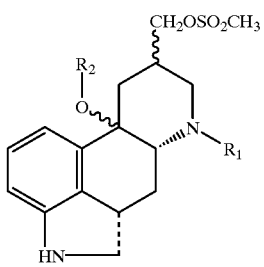

wherein $R_1$, $R_2$ and—are as defined above, with KCN, (4) reacting with an acid the resulting compound represented by formula V

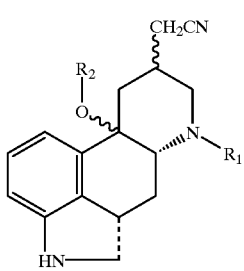

wherein $R_1$, and $R_2$, and—are as defined above, in the presence of an alcohol represented by the formula $R_5$-OH, wherein $R_5$ is as above defined;

(5) reducing the resultant compound of formula VI

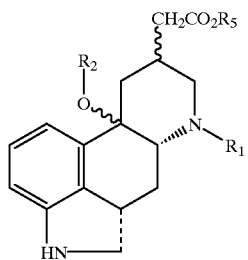

VI wherein $R_1$, $R_2$, $R_5$ and—are as defined above, and, optionally, converting the resulting compound of formula I wherein Z is $CH_2CH_2OH$ or $CH_2OH$, as obtained above under step (1), into a pharmaceutically acceptable salt thereof.

8. A process for preparing ergoline derivative of claim 4, wherein Z is $CH_2CH_2CH_2OH$, or a pharmaceutically acceptable salt thereof, which comprises:

(1) condensing a compound represented by formula IV

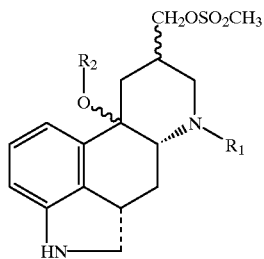

IV with a di-$C_1$–$C_5$-alkylmalonate salt;

(2) heating the resulting compound represented by formula VII:

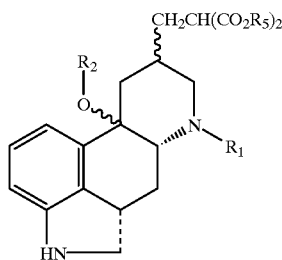

VII wherein $R_1$, $R_2$, $R_5$ and—are as defined above, (3) reducing the resulting compound represented by formula VIII:

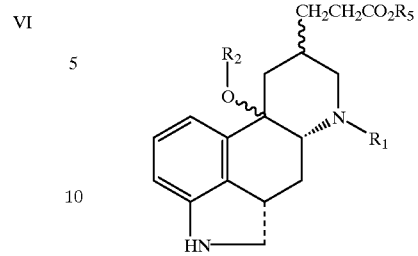

VIII wherein $R_1$, $R_2$, $R_5$ and—are as defined above, and, optionally, converting the resulting compound of formula I into a pharmaceutically acceptable salt thereof.

9. A process for preparing the ergoline derivative of claim 4, wherein Z is a group of formula ($C(R_4)_2OH$, wherein $R_4$ is as defined in claim 4, or a pharmaceutically acceptable salt thereof, which comprises:

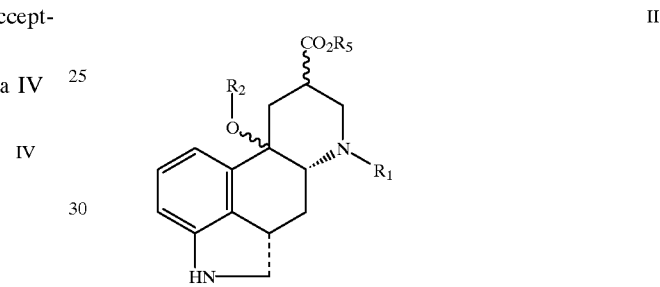

II with a Grignard reagent represented by the formula $R_4MgBr$ wherein $R_4$ is as defined above, and optionally, converting the resulting compound represented by formula I into a pharmaceutically acceptable salt thereof.

10. A process for preparing the ergoline derivative of claim 4, wherein—at 8, 9 position is a single bond, which comprises converting a compound represented by formula IX

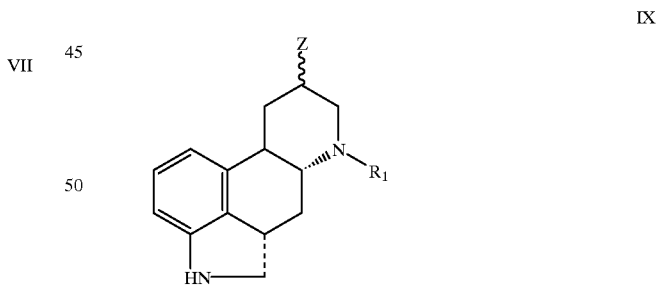

IX wherein—, $R_1$ and Z are as defined in claim 4, by photochemical addition of a compound represented by formula $R_2$-OH, wherein $R_2$ is as defined in claim 4, in the presence of an acid, and, optionally, converting the resulting compounds represented by formula I into a pharmaceutically acceptable salt thereof.

11. A pharmaceutically composition which comprises, as an active ingredient, a therapeutically effective amount of an ergoline represented by formula I as defined in claim 4, or a pharmaceutically acceptable salt thereof, in admixture with a pharmaceutically acceptable carrier or diluent.

12. A method of treating neurodegenerative diseases, comprising administering to a patient in need thereof an effective amount of the ergoline derivative of formula I as defined in claim 4 or a pharmaceutically acceptable salt thereof.

* * * * *

UNITED STATES PATENT AND TRADEMARK OFFICE
CERTIFICATE OF CORRECTION

PATENT NO. : 6,060,483

DATED : May 9, 2000

INVENTOR(S): Sergio MANTEGANI, et al.

It is certified that an error appears in the above-identified patent and that said Letters Patent is hereby corrected as shown below:

On the Title page, item [22] the PCT Filing Date is incorrectly listed. It should read as follows:

--[22]  PCT Filed:  May 29, 1997--

Signed and Sealed this

Third Day of April, 2001

Attest:

NICHOLAS P. GODICI

*Attesting Officer*      *Acting Director of the United States Patent and Trademark Office*